(12) United States Patent
Coleman et al.

(10) Patent No.: US 7,187,963 B2
(45) Date of Patent: Mar. 6, 2007

(54) BIDIRECTIONAL CATHETER HAVING MAPPING ASSEMBLY

(75) Inventors: James H. Coleman, Rialto, CA (US); Kristine B. Fuimaono, Covina, CA (US); Michel Haissaguerre, Talence (FR)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 10/746,811

(22) Filed: Dec. 24, 2003

(65) Prior Publication Data

US 2004/0143175 A1    Jul. 22, 2004

Related U.S. Application Data

(63) Continuation of application No. 10/107,899, filed on Mar. 25, 2002, now Pat. No. 6,795,721, which is a continuation-in-part of application No. 09/551,467, filed on Apr. 17, 2000, now Pat. No. 6,628,976.

(60) Provisional application No. 60/178,478, filed on Jan. 27, 2000.

(51) Int. Cl.
*A61B 5/042*    (2006.01)

(52) U.S. Cl. .................. 600/374; 600/381; 606/41; 607/122

(58) Field of Classification Search ................ 600/374, 600/381; 606/41, 49; 607/122
See application file for complete search history.

(56) References Cited

U.S. PATENT DOCUMENTS 4,203,430 A    5/1980   Takahashi (Continued)

FOREIGN PATENT DOCUMENTS

EP    0 499 491 A2    8/1992

(Continued)

OTHER PUBLICATIONS

M. Haissaguerre et al., "Spontaneous Initiation of Atrial Fibrillation by Ectopic Beats Originating in the Pulmonary Veins", The New England Journal of Medicine, 339:659-666 Sep. 3, 1998.

*Primary Examiner*—Lee S. Cohen
(74) *Attorney, Agent, or Firm*—Christie, Parker & Hale, LLP.

(57)    ABSTRACT

A bidirectional mapping catheter is provided. The catheter comprises an elongated flexible tubular catheter body having an axis and proximal and distal ends. A mapping assembly, which is mounted at the distal end of the tubular body, has a preformed generally circular main region having an outer surface that is generally transverse to the axis of the catheter body. The generally circular main region has proximal and distal ends and carries a plurality of spaced apart electrodes. An electrode lead wire is associated with each electrode. Each electrode lead wire has proximal and distal ends and extends through the catheter body and into the mapping assembly. The distal end of each electrode lead wire is electrically connected to its associated electrode. First and second puller wires are provided. Each puller wire has proximal and distal ends and extends through the tubular catheter body. The distal end of each puller wire is anchored at or near the distal end of the catheter body. A handle is connected to the proximal ends of the catheter body and puller wires for moving the puller wires longitudinally relative to the catheter body. Longitudinal movement of a puller wire relative to the catheter body results in deflection of the distal end of the catheter body.

20 Claims, 13 Drawing Sheets

U.S. PATENT DOCUMENTS

| | | | |
|---|---|---|---|
| 4,207,873 A | 6/1980 | Kruy | |
| 4,777,955 A | 10/1988 | Brayton et al. | |
| 4,882,777 A | 11/1989 | Narula | |
| 4,920,980 A | 5/1990 | Jackowski | |
| 4,960,134 A | 10/1990 | Webster, Jr. | |
| 4,984,581 A | 1/1991 | Stice | |
| 5,170,787 A | 12/1992 | Lindegren | |
| 5,255,679 A | 10/1993 | Imran | |
| 5,263,493 A | 11/1993 | Avitall | |
| 5,275,162 A | 1/1994 | Edwards et al. | |
| 5,327,905 A | 7/1994 | Avitall | |
| 5,354,297 A | 10/1994 | Avitall | |
| 5,383,923 A | 1/1995 | Webster, Jr. | |
| 5,445,148 A | 8/1995 | Jaraczewski et al. | |
| 5,456,664 A | 10/1995 | Heinzelman et al. | |
| 5,462,544 A | 10/1995 | Saksena et al. | |
| 5,487,385 A | 1/1996 | Avitall | |
| 5,545,200 A | 8/1996 | West et al. | |
| 5,549,581 A | 8/1996 | Lurie et al. | |
| 5,582,609 A | 12/1996 | Swanson et al. | |
| 5,617,854 A | 4/1997 | Munsif | |
| 5,626,136 A | 5/1997 | Webster, Jr. | |
| 5,642,736 A | 7/1997 | Avitall | |
| 5,656,030 A | 8/1997 | Hunjan et al. | |
| 5,673,695 A | 10/1997 | McGee et al. | |
| 5,680,860 A | 10/1997 | Imran | |
| 5,730,127 A | 3/1998 | Avitall | |
| 5,755,760 A | 5/1998 | Maguire et al. | |
| 5,797,905 A | 8/1998 | Fleischman et al. | |
| 5,800,428 A | 9/1998 | Nelson et al. | |
| 5,823,955 A | 10/1998 | Kuck et al. | |
| 5,827,278 A | 10/1998 | Webster, Jr. | |
| 5,836,947 A | 11/1998 | Fleischman et al. | |
| 5,860,920 A | 1/1999 | McGee et al. | |
| 5,865,800 A | 2/1999 | Mirarchi et al. | |
| 5,879,295 A | 3/1999 | Li et al. | |
| 5,882,333 A | 3/1999 | Schaer et al. | |
| 5,882,346 A | 3/1999 | Pomeranz et al. | |
| 5,931,811 A | 8/1999 | Haissaguerre et al. | |
| 5,935,102 A | 8/1999 | Bowden et al. | |
| 5,938,694 A | 8/1999 | Jaraczewski et al. | |
| 5,951,471 A | 9/1999 | de la Rama et al. | |
| 5,984,909 A | 11/1999 | Lurie et al. | |
| 5,997,526 A | 12/1999 | Giba et al. | |
| 6,002,955 A | 12/1999 | Willems et al. | |
| 6,035,224 A | 3/2000 | West | |
| 6,064,902 A | 5/2000 | Haissaguerre et al. | |
| 6,088,614 A | 7/2000 | Swanson | |
| 6,090,104 A | 7/2000 | Webster, Jr. | |
| 6,096,036 A | 8/2000 | Bowe et al. | |
| 6,106,522 A | 8/2000 | Fleischman et al. | |
| 6,120,476 A * | 9/2000 | Fung et al. | 607/122 |
| 6,123,699 A | 9/2000 | Webster, Jr. | |
| 6,129,724 A | 10/2000 | Fleischman et al. | |
| 6,141,576 A | 10/2000 | Littmann et al. | |
| 6,146,381 A | 11/2000 | Bowe et al. | |
| 6,169,916 B1 | 1/2001 | West | |
| 6,171,277 B1 | 1/2001 | Ponzi | |
| 6,183,463 B1 | 2/2001 | Webster, Jr. | |
| 6,219,582 B1 | 4/2001 | Hofstad et al. | |
| 6,325,797 B1 | 12/2001 | Stewart et al. | |
| 6,468,260 B1 * | 10/2002 | Bumbalough et al. | 604/523 |
| 6,542,781 B1 | 4/2003 | Koblish et al. | |
| 6,628,976 B1 | 9/2003 | Fuimaono et al. | |
| 6,711,428 B2 | 3/2004 | Fuimaono et al. | |
| 6,795,721 B2 | 9/2004 | Coleman et al. | |
| 6,804,545 B2 | 10/2004 | Fuimaono et al. | |
| 6,845,257 B2 | 1/2005 | Fuimaono et al. | |
| 6,987,996 B2 | 1/2006 | Fuimaono et al. | |
| 2003/0191380 A1 | 10/2003 | Fuimaono et al. | |
| 2003/0199746 A1 | 10/2003 | Fuimaono et al. | |
| 2004/0158139 A1 | 8/2004 | Fuimaono et al. | |
| 2004/0158140 A1 | 8/2004 | Fuimaono et al. | |

FOREIGN PATENT DOCUMENTS

| | | |
|---|---|---|
| EP | 0 928 601 A1 | 7/1999 |
| EP | 0 985 423 A2 | 3/2000 |
| EP | 1050316 * | 11/2000 |
| WO | WO 95/10225 | 4/1995 |

* cited by examiner

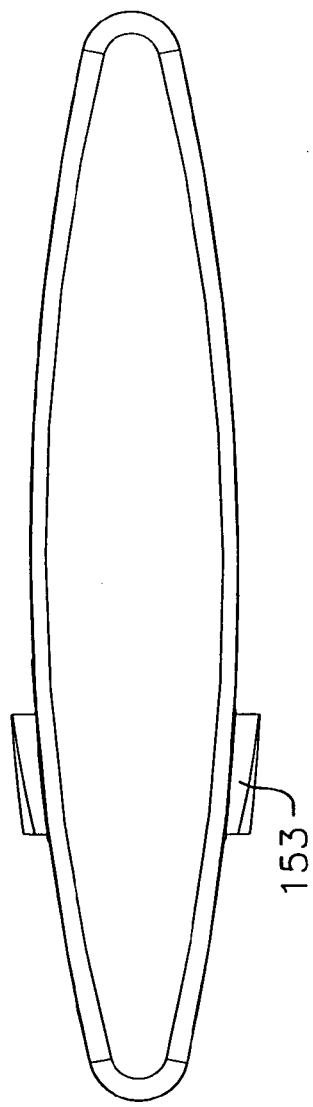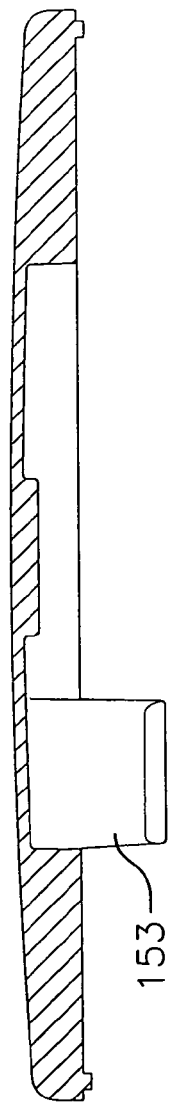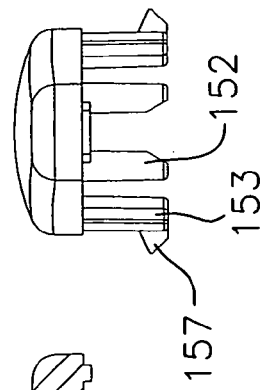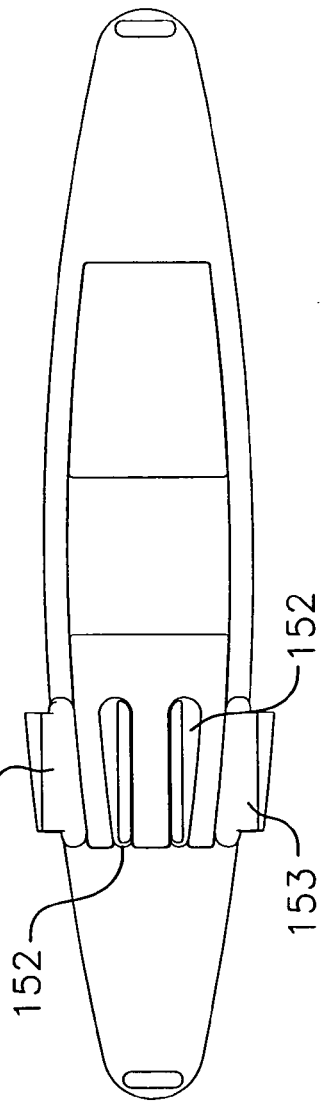

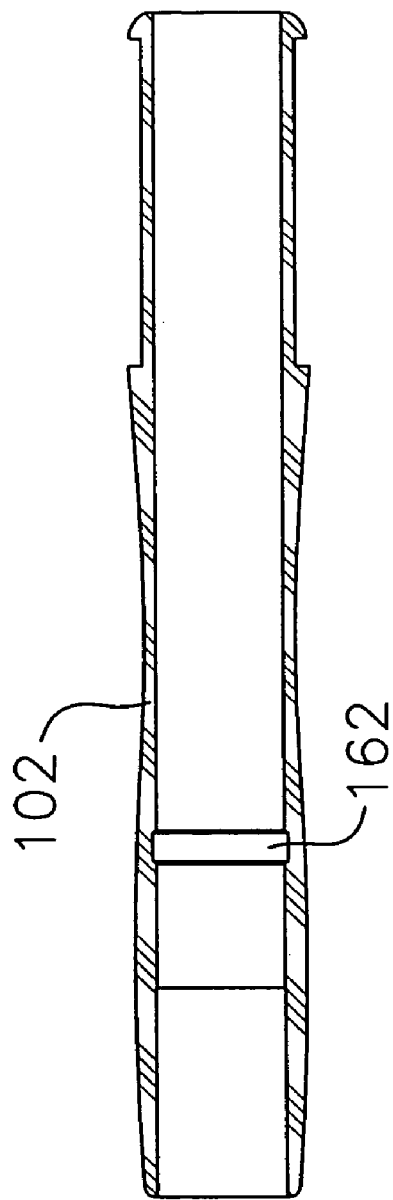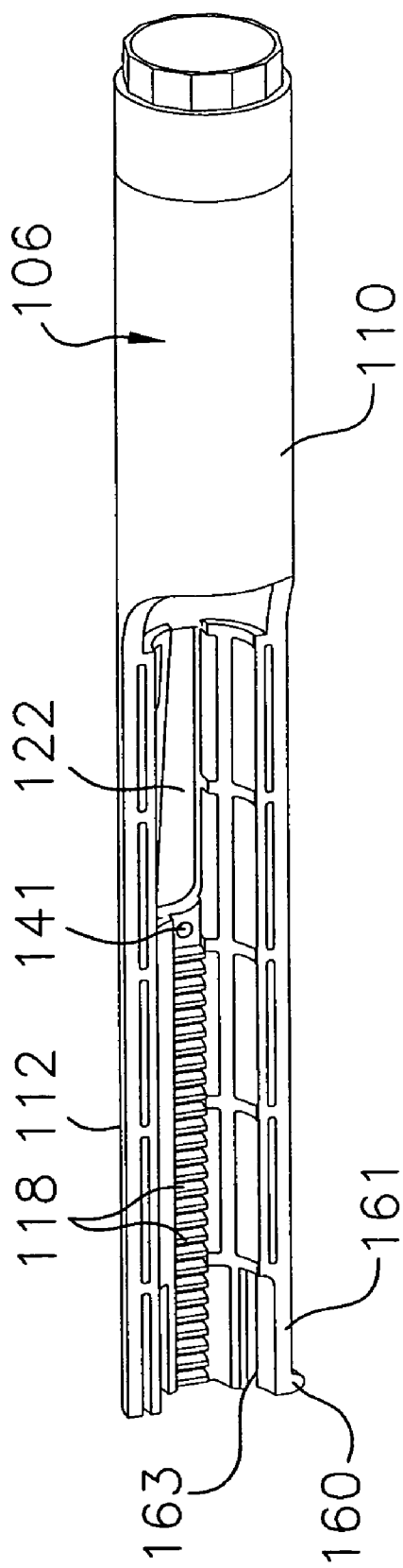

BIDIRECTIONAL CATHETER HAVING MAPPING ASSEMBLY

CROSS-REFERENCE TO RELATED APPLICATIONS

This application is a continuation of application Ser. No. 10/107,899, filed Mar. 25, 2002 U.S. Pat. No. 6,795,721, entitled BIDIRECTIONAL CATHETER HAVING MAPPING ASSEMBLY, issued Sep. 21, 2004, which is a continuation-in-part of U.S. application Ser. No. 09/551,167, filed Apr. 17, 2000 U.S. Pat. No. 6,628,976, issued Sep. 30, 2003, which claims the benefit of U.S. Provisional Application Ser. No. 60/178,478, filed Jan. 27, 2000, the entire disclosures of which are incorporated herein by reference.

FIELD OF THE INVENTION

The present invention relates to an improved bidirectional mapping catheter that is particularly useful for mapping electrical activity in a tubular region of or near the heart.

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination. None of the proposed techniques, however, provide for measurement of the activity within a pulmonary vein, coronary sinus or other tubular structure about the inner circumference of the structure.

SUMMARY OF THE INVENTION

The present invention is directed to a bidirectional catheter having a mapping assembly and a method for measuring electrical activity within a tubular region of or near the heart, e.g., a pulmonary vein, the coronary sinus, the superior vena cava, or the pulmonary outflow tract. The mapping assembly, which has a generally circular region with a series of spaced-apart electrodes mounted thereon, is positioned within the tubular region so that the electrodes are in contact with an inner generally circumferential surface inside the tubular structure.

In one embodiment, the invention is directed to a bidirectional mapping catheter. The catheter comprises an elongated flexible tubular catheter body having an axis and proximal and distal ends. A mapping assembly, which is mounted at the distal end of the tubular body, has a preformed generally circular main region having an outer surface. The generally circular main region is generally transverse to the axis of the catheter body, has proximal and distal ends and carries a plurality of spaced apart electrodes. An electrode lead wire is associated with each electrode. Each electrode lead wire has proximal and distal ends and extends through the catheter body and into the mapping assembly. The distal end of each electrode lead wire is electrically connected to its associated electrode. First and second puller wires are provided. Each puller wire has proximal and distal ends and extends through the tubular catheter body. The distal end of each puller wire is anchored at or near the distal end of the catheter body. A handle is connected to the proximal ends of the catheter body and puller wires for moving the puller wires longitudinally relative to the catheter body. Longitudinal movement of a puller wire relative to the catheter body results in deflection of the distal end of the catheter body.

In another embodiment, the invention is directed to a method for mapping electrical activity within a tubular region of or near the heart having a inner circumference. The method comprising inserting into the heart the distal end of a catheter as generally described above. The outer circumference of the generally circular main region is contacted with the inner circumference of the tubular region. The electrical activity within the tubular region is mapped with the at least one electrode along the generally circular main region.

DESCRIPTION OF THE DRAWINGS

These and other features and advantages of the present invention will be better understood by reference to the following detailed description when considered in conjunction with the accompanying drawings wherein:

FIG. 14 is a top view of a fastener for use with the inventive handle.

FIG. 15 is a side view of a fastener for use with the inventive handle.

FIG. 16 is a bottom view of a fastener for use with the inventive handle.

FIG. 17 is an end view of a fastener for use with the inventive handle.

FIG. 18 is a side cross-sectional view of the inside of the handle housing.

FIG. 19 is a side perspective view of an alternative embodiment of the primary piston.

DETAILED DESCRIPTION

Figure 1:
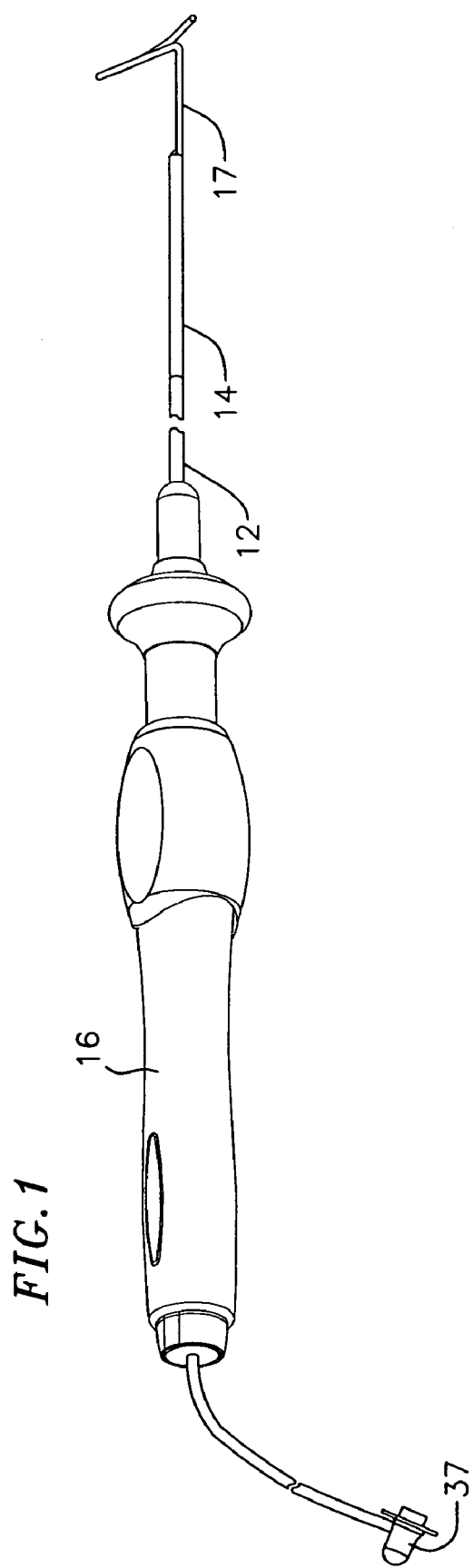
FIG. 1 is a side view of an embodiment of the catheter of the invention.

In a particularly preferred embodiment of the invention, there is provided a catheter having a mapping assembly at its distal end. In the embodiment shown in FIG. 1, the catheter comprises an elongated catheter body 12 having proximal and distal ends, an intermediate section 14 at the distal end of the catheter body, a control handle 16 at the proximal end of the catheter body, and a mapping assembly 17 mounted at the distal end of the catheter to the intermediate section. If desired, the intermediate section 14 can be eliminated, and the mapping assembly 17 can be mounted directly to the distal end of the catheter body 12.

Figure 2:
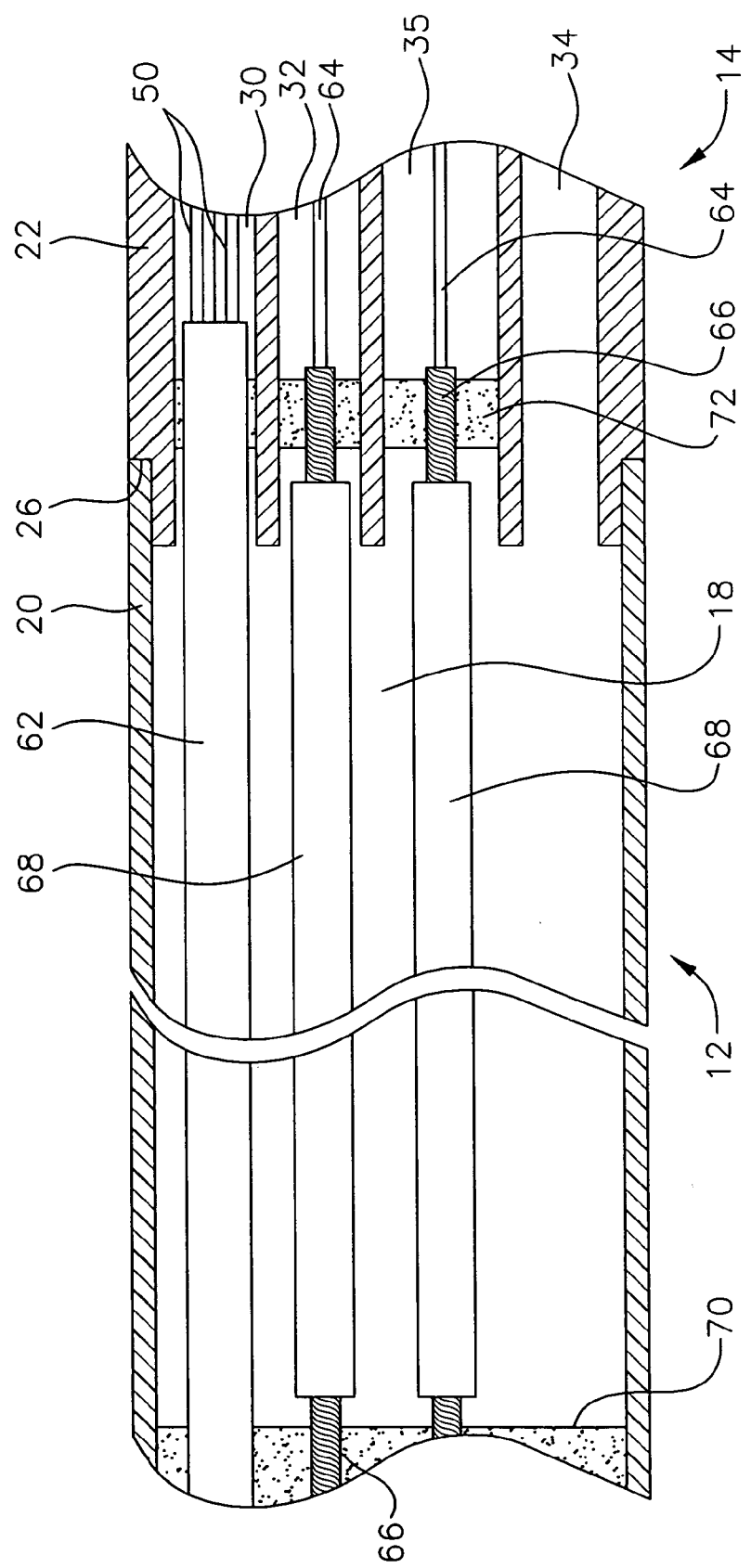
FIG. 2 is a side cross-sectional view of a catheter body according to the invention, including the junction between the catheter body and intermediate section.

With reference to FIG. 2, the catheter body 12 comprises an elongated tubular construction having a single, axial or central lumen 18, although additional lumens can be added as desired. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate a puller wire, lead wires, and any other desired wires, cables or tubes. If desired, the inner surface of the outer wall 20 is lined with a stiffening tube (not shown) to provide improved torsional stability. A particularly preferred catheter has an outer wall 20 with an outer diameter of from about 0.090 inch to about 0.94 inch and an inner diameter of from about 0.061 inch to about 0.065 inch.

The intermediate section 14 comprises a short section of tubing 22 having four lumens. The first lumen 30 electrode carries lead wires 50, the second lumen 32 carries a puller wire 64, and the third lumen 34 carries a support member 24 and the fourth lumen 35 carries another puller wire 64, all of which are discussed further below. The tubing 22 is made of a suitable non-toxic material that is preferably more flexible than the catheter body 12. A presently preferred material for the tubing 22 is braided polyurethane, i.e., polyurethane with an embedded mesh of braided stainless steel or the like. The size of each lumen is not critical, but is sufficient to house the lead wires, puller wire or support member.

The useful length of the catheter, i.e., that portion that can be inserted into the body excluding the mapping assembly 17, can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIG. 2. The proximal end of the intermediate section 14 comprises an outer circumferential notch 26 that receives the inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

At the distal end of the intermediate section 14 is a mapping assembly 17, as shown in FIGS. 3 to 7. In the depicted embodiment, the mapping assembly comprises a support member 24 covered by a non-conductive covering 28, and the mapping assembly has a generally straight proximal region 38, a generally circular main region 39 and a generally straight distal region 40. However, if desired, the generally straight distal region 40 can be eliminated.

The proximal region 38 is mounted on the intermediate section 14, as described in more detail below, so that its axis is generally parallel to the axis of the intermediate section. The proximal region 38 preferably has an exposed length, e.g., not contained within the intermediate section 14, ranging from about 3 mm to about 12 mm, more preferably about 3 mm to about 8 mm, still more preferably about 5 mm, but can vary as desired.

The generally circular main region 39 has an outer diameter preferably ranging from about 8 mm to about 35 mm, more preferably from about 10 mm to about 25 mm, still more preferably from about 12 mm to about 20 mm. The generally circular main region 39 does not have to form a complete circle, but should be at least about 180°, e.g., a semi-circle, more preferably at least about 270°, still more preferably at least about 320°. In a preferred embodiment, the generally circular main region 39 forms at least a complete circle, e.g., is at least 360°. If desired, the generally circular main region 39 can comprise more than one loop or circle, so that it has, for example, a spiral or conical shape.

Figure 4:
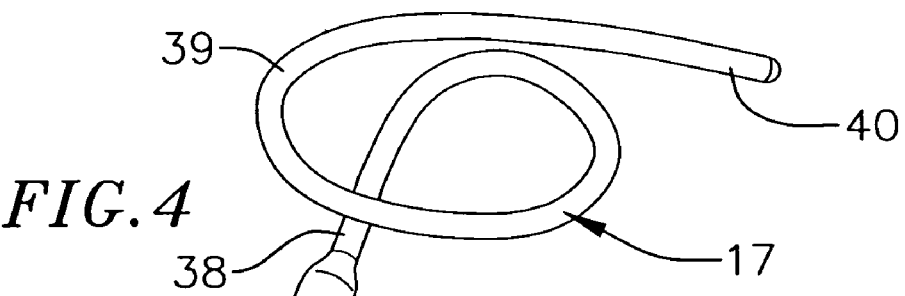
FIG. 4 is a schematic perspective view of the mapping assembly according to the invention.
Figure 5:
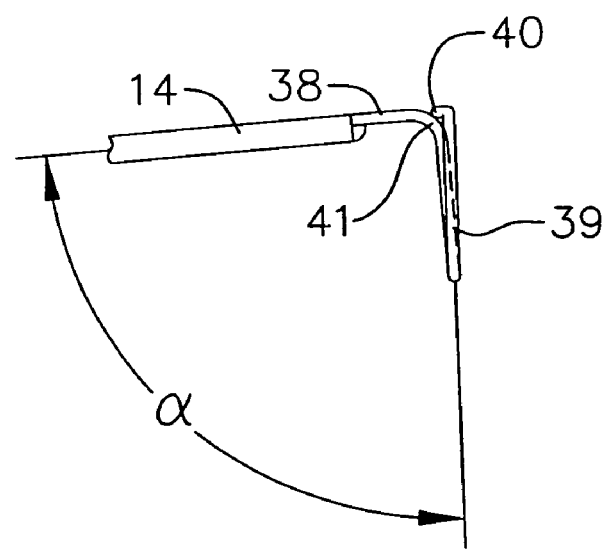
FIG. 5 is a side view of the mapping assembly according to the invention in a clockwise formation.
Figure 6:
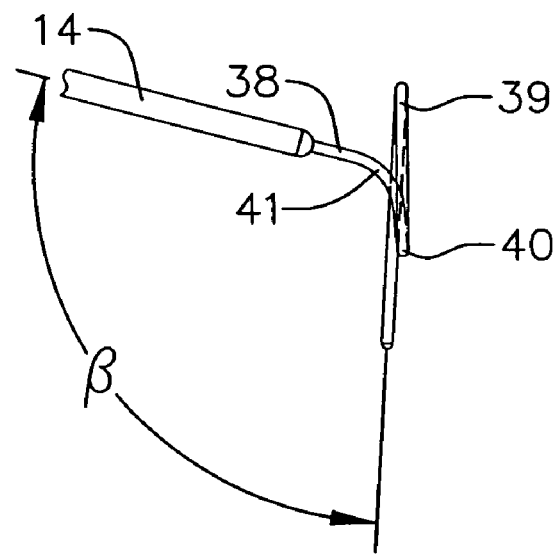
FIG. 6 is a side view of the mapping assembly according to the invention in a counterclockwise formation rotated 90° relative to the assembly depicted in FIG. 5.

Preferably the generally circular main region 39 does not form a flat circle, but is very slightly helical, as shown in FIGS. 4 to 6. In a preferred embodiment, the transition region 41 of the straight proximal region 38 and generally circular main region 39 is slightly curved and formed such that, when viewed from the side with the proximal region at the top of the circular main region as shown in FIG. 5, the proximal region (along with the intermediate section 14) forms an angle α with the curved region ranging from about 75° to about 95°, preferably from about 83° to about 93°, more preferably about 87°. The main region 39 can curve in a clockwise direction, as shown in FIG. 5, or a counter-clockwise direction, as shown in FIG. 6. When the assembly 17 is turned 90°, as shown in FIG. 6, so that the transition region 41 is near the center of the main region, the proximal region (along with the intermediate section 14) forms an angle β with the main region ranging from about 90° to about 135°, preferably from about 100° to about 110°, more preferably about 105°.

The support member 24 is preferably made of a material having shape-memory, i.e., that can be straightened or bent out of its original shape upon exertion of a force and is capable of substantially returning to its original shape upon removal of the force. A particularly preferred material for the support member 24 is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. The non-conductive covering 28 can be made of any suitable material, and is preferably made of a biocompatible plastic such as polyurethane or PEBAX. If desired, the support member 24 can be eliminated and the distal end of the non-conductive covering 28 can be preformed to have the desired curve of the mapping assembly 17.

A series of ring electrodes 36 are mounted on the non-conductive covering 28 of the generally circular main region 39 of the mapping assembly 17. The ring electrodes 36 can be made of any suitable solid conductive material, such as platinum or gold, preferably a combination of platinum and iridium, and mounted onto the non-conductive covering 28 with glue or the like. Alternatively, the ring electrodes can be formed by coating the non-conductive covering 28 with an electrically conducting material, like platinum, gold and/or iridium. The coating can be applied using sputtering, ion beam deposition or an equivalent technique. In another alternative embodiment, the ring electrodes can be formed by repeatedly wrapping an end of an electrode lead wire around the non-conductive covering 28 and stripping off the coating of the lead wire to expose a conductive surface. Other methods for forming ring electrodes 36 on the non-conductive covering 28 can also be used in accordance with the invention.

In a preferred embodiment, each ring electrode 36 is mounted by first forming a hole in the non-conductive covering 28. An electrode lead wire 50 is fed through the hole, and the ring electrode 36 is welded in place over the lead wire and non-conductive covering 28. The lead wires 50 extend between the non-conductive covering 28 and the support member 24. The proximal end of each lead wire 50 is electrically connected to a suitable connector 37, which is connected to a suitable monitor (not shown).

Figure 7:
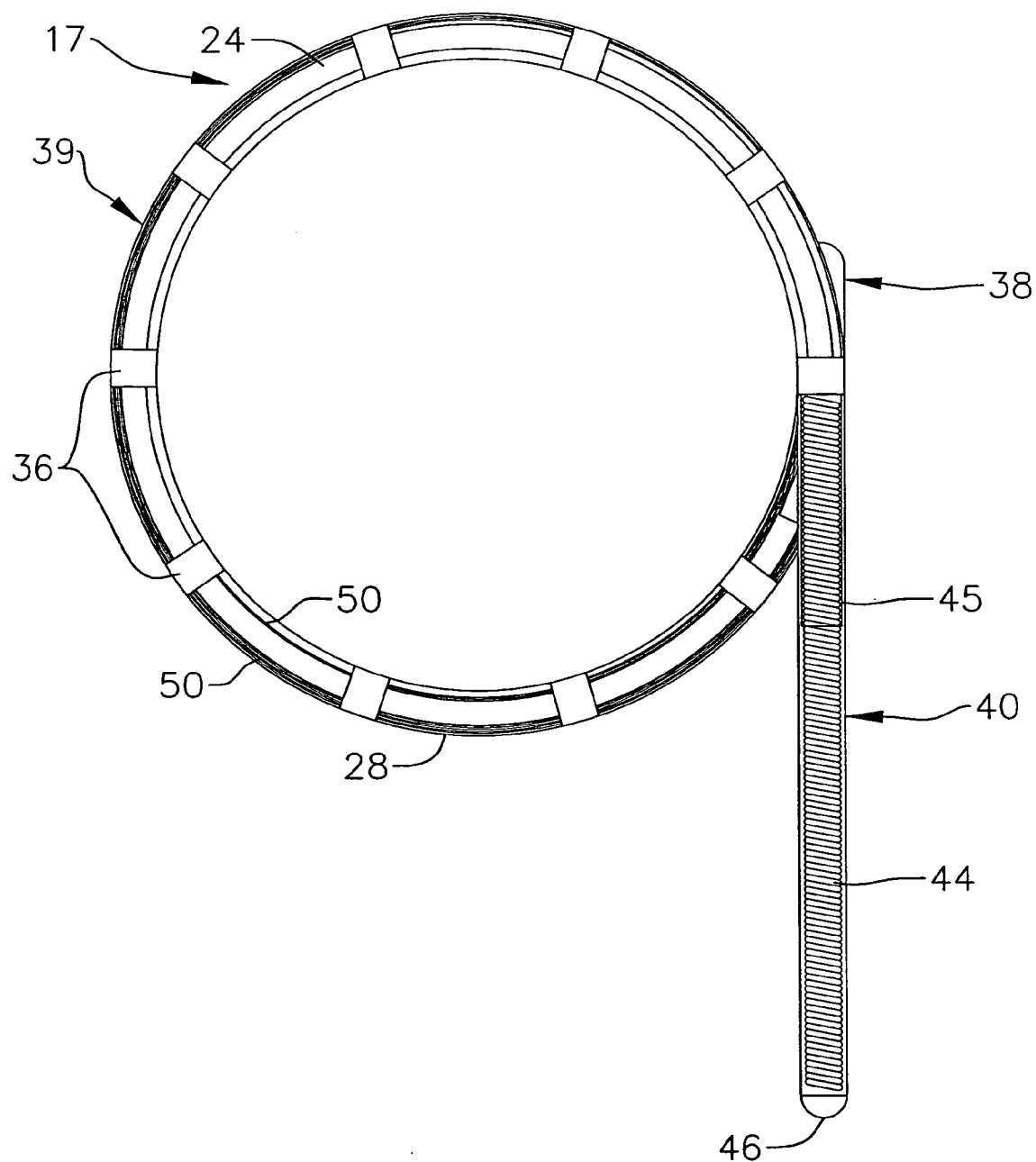
FIG. 7 is a schematic view of the mapping assembly according to the invention.

The number of ring electrodes 36 on the assembly can vary as desired. Preferably the number of ring electrodes ranges from about six to about twenty, preferably from about eight to about twelve. In a particularly preferred embodiment, the assembly carries ten ring electrodes. The ring electrodes 36 are preferably approximately evenly spaced around the generally circular main region 39, as best shown in FIG. 7. In a particularly preferred embodiment, a distance of approximately 5 mm is provided between the centers of the ring electrodes 36.

Figure 8:
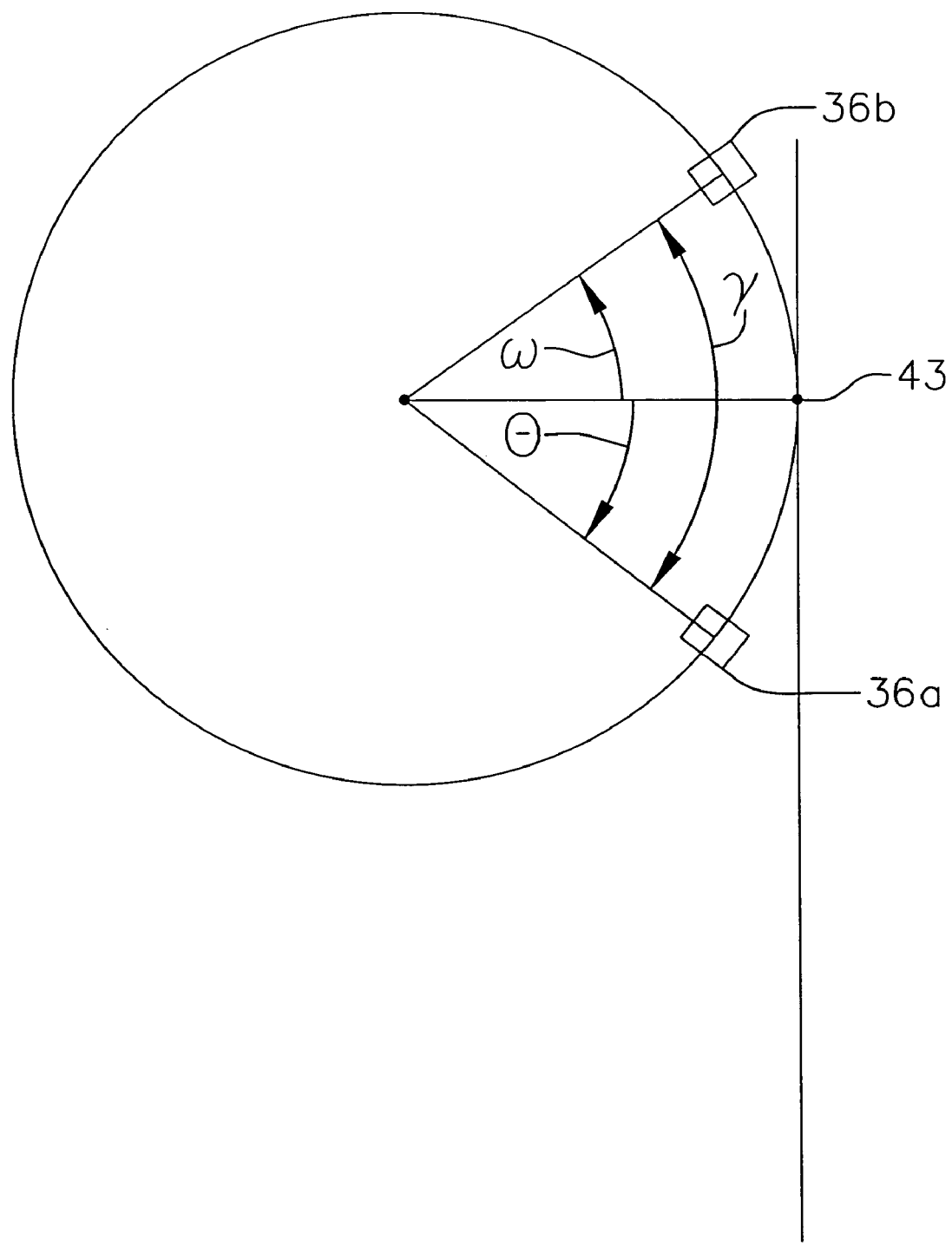
FIG. 8 is a schematic view of the mapping assembly according to the invention depicting the relationship between the first and last electrodes.

FIGS. 7 and 8 show a particularly preferred electrode arrangement. As explained above, the generally circular main region 39 is very slightly helical, although FIGS. 7 and 8 depict the main region as a flat circle, as it would generally appear when viewed from the distal end of the catheter. The generally straight distal region 40 forms a tangent relative to the generally circular main region 39 and contacts the main region at a tangent point 43. A first electrode 36a is provided, which is the electrode that is on the generally circular main region 39 closest to the proximal region 38. A second electrode 36b is provided, which is the electrode that is on the generally circular main region 39 closest to the distal region 40. Preferably, the first electrode 36a is positioned along the circumference of the generally circular main region 39 at a distance $\theta$ of no more than about 55° from the tangent point, more preferably no more than about 48° from the tangent point, still more preferably from about 15° to about 36° from the tangent point. Preferably the second electrode 36b is positioned along the circumference of the generally circular main region 39 at a distance $\omega$ of no more than about 55° degrees from the tangent point, more preferably no more than about 48° from the tangent point, still more preferably from about 15° to about 36° from the tangent point. Preferably the first electrode 36a is positioned along the circumference of the generally circular main region 39 at a distance $\gamma$ of no more than 100° from the second electrode 36b, preferably no more than 80° from the second electrode, still more preferably from about 30° to about 75° from the second electrode.

If desired, additional electrodes (not shown) could be mounted along the intermediate section 14, the generally straight proximal section 39, the transition region 41, and generally straight distal region 40.

Preferably the generally straight distal region 40 is provided with an atraumatic design to prevent the distal end of the mapping assembly 17 from penetrating tissue. In the depicted embodiment, the distal region 40 comprises a tightly wound coil spring 44 made, for example, of stainless steel, such as the mini guidewire commercially available from Cordis Corporation (Miami, Fla.) or a coil having a 0.0045 inch wire size and a 0.009 inch inner diameter, such as that commercially available from Microspring. The coil spring 44 is mounted at its proximal end in a short piece of tubing 45 with polyurethane glue or the like, which is then glued or otherwise anchored within the non-conductive covering 28. The tubing 45 is less flexible than the non-conductive covering 28 but more flexible than the support member 24 to provide a transition in flexibility along the length of the mapping assembly 17. The distal end of the distal region 40 is capped, preferably with polyurethane glue 46, to prevent body fluids from entering the mapping assembly 17. In the depicted embodiment, the generally straight distal region 40 has a length of about 0.5 inch, but can be any desired length, for example, ranging from about 0.25 inch to about 1.0 inch. The generally straight distal region 40 is preferably sufficiently long to serve as an anchor for introducing the catheter into a guiding sheath, as discussed in more detail below, because the mapping assembly 17 must be straightened upon introduction into the sheath. Without having the generally straight distal region 40 as an anchor, the mapping assembly 17 has a tendency to pull out of the guiding sheath upon its introduction into the guiding sheath. Additionally, if desired, the distal region 40 can be formed, at least in part, of a radiopaque material to aid in the positioning of the mapping assembly 17 under fluoroscopy.

Figure 3:
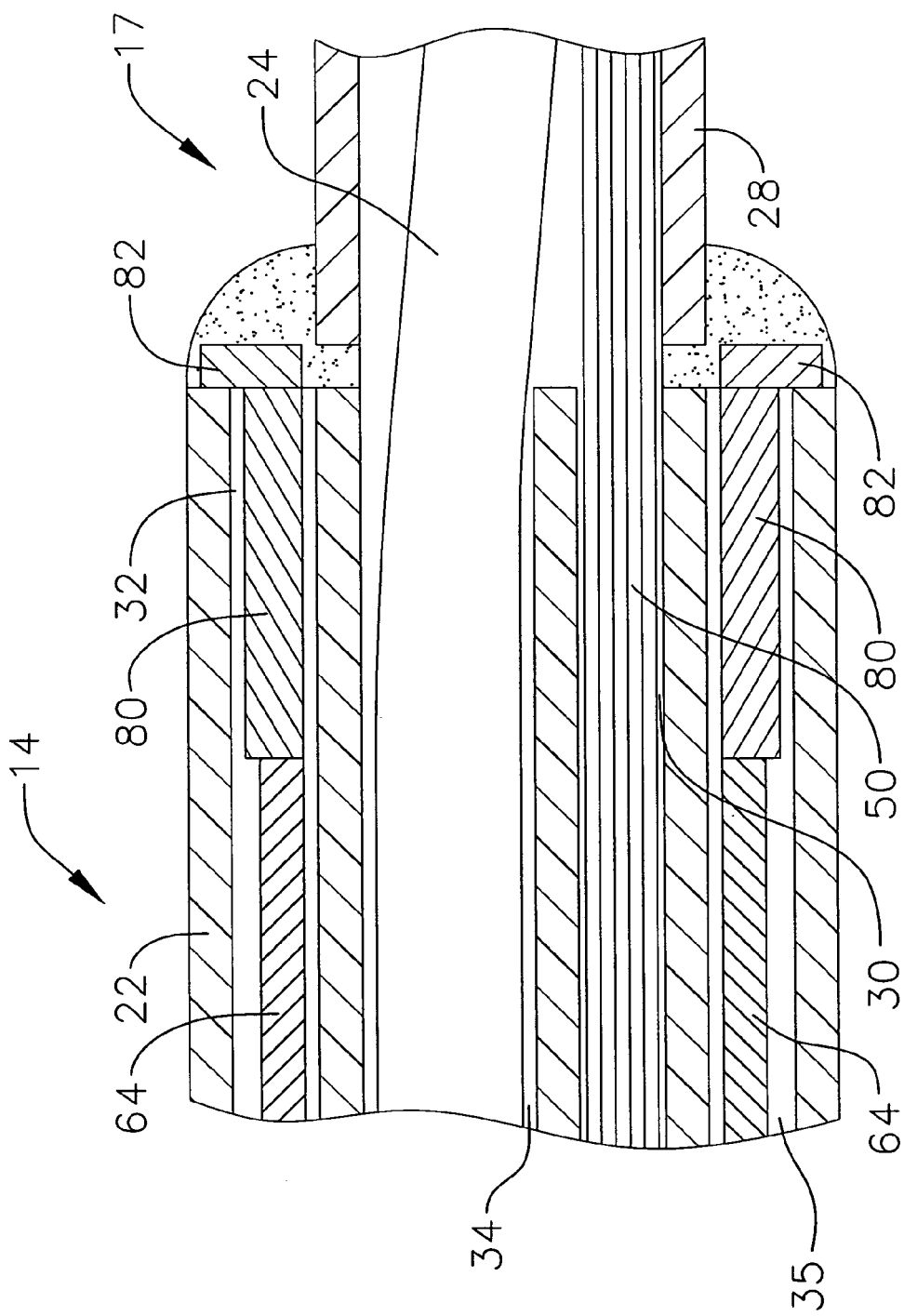
FIG. 3 is a cross-sectional view of the intermediate section, including the junction between the intermediate section and the mapping assembly.

The junction of the intermediate section 14 and mapping assembly 17 is shown in FIG. 3. The non-conductive covering 28 is attached to the tubing 22 of the intermediate section by glue or the like. The support member 24 extends from the third lumen 32 into the non-conductive covering 28. The proximal end of the support member 24 terminates a short distance within the third lumen 32, approximately about 5 mm, so as not to adversely affect the ability of the intermediate section 14 to deflect. However, if desired, the proximal end of the support member 24 can extend into the catheter body 12.

The lead wires 50 attached to the ring electrodes 36 extend through the first lumen 30 of the intermediate section 14, through the central lumen 18 of the catheter body 12, and the control handle 16, and terminate at their proximal end in the connector 37. As shown in the depicted embodiment, the portion of the lead wires 50 extending through the central lumen 18 of the catheter body 12, control handle 16 and proximal end of the intermediate section 14 are preferably enclosed within a protective sheath 62, which can be made of any suitable material, preferably polyimide. The protective sheath 62 is anchored at its distal end to the proximal end of the intermediate section 14 by gluing it in the first lumen 30 with polyurethane glue or the like.

Two puller wires 64 are provided for deflection of the intermediate section 14. Each puller wire 64 extends through the catheter body 12, is anchored at its proximal end to the control handle 16, and is anchored at its distal end to the intermediate section 14. If the intermediate section 14 is eliminated, the distal ends of the puller wires 64 are anchored at or near the distal end of the catheter body 12. The puller wires 64 are made of any suitable metal, such as stainless steel or Nitinol, and are preferably coated with Teflon® or the like. The coating imparts lubricity to the puller wires 64. Each puller wire 64 preferably has a diameter ranging from about 0.006 to about 0.010 inch.

Two compression coils 66 are situated within the catheter body 12, each in surrounding relation to a corresponding puller wire 64. The compression coils 66 extend from the proximal end of the catheter body 12 to the proximal end of the intermediate section 14. Each compression coil 66 is made of any suitable metal, preferably stainless steel. Each compression coil 66 is tightly wound on itself to provide flexibility, i.e., bending, but to resist compression. The inner diameter of each compression coil 66 is preferably slightly larger than the diameter of its corresponding puller wire 64. The Teflon® coating on the puller wires 64 allows them to slide freely within the compression coils 66. As shown in the depicted embodiment, the outer surface of each compression coil 66 is preferably covered by a flexible, non-conductive sheath 68, e.g., made of polyimide tubing.

Each compression coil 66 is anchored at its proximal end to the outer wall 20 of the catheter body 12 at proximal glue joint 70 and at its distal end to the intermediate section 14 at distal glue joint 72. Both glue joints 70 and 72 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the compression coil 66 and wicks around the outer circumference to form a glue joint about the entire circumference of the compression coil.

As noted above, in the depicted embodiment one puller wire 64 extends into the second lumen 32 of the intermediate section 14 and the other puller wire extends into the fourth lumen 35 of the intermediate section. Preferably each puller wire 64 is anchored at its distal end to the distal end of the intermediate section 14, as shown in FIG. 3. A preferred mechanism for anchoring a puller wire 64 to the intermediate section 14 comprises a T-shaped anchor, which comprises a short piece of tubular stainless steel 80, e.g., hypodermic stock, that is fitted over the distal end of the puller wire 64 and crimped to fixedly secure it to the puller wire. The distal end of the tubular stainless steel 80 is fixedly attached, e.g., by welding, to a cross-piece 82 formed of stainless steel ribbon or the like. The cross-piece 82 sits beyond the distal end of the lumen through which the corresponding puller wire extends (i.e., the second lumen 32 or fourth lumen 35). The cross-piece 82 is larger than the lumen opening and, therefore, cannot be pulled through the opening. The distal end of the each puller wire lumen 32 and 35 is then filled with glue or the like, preferably a polyurethane glue. Within the lumens 32 and 35 of the intermediate section 14, the puller wires 64 preferably each extend through a plastic, e.g., Teflon®, puller wire sheath (not shown), which prevents the corresponding puller wire 64 from cutting into the wall of the intermediate section when the intermediate section is deflected. Any other method for anchoring the puller wires 64 to the intermediate section 14 or catheter body 12 can be used in accordance with the invention.

In the depicted embodiment, the puller wires 64 are anchored on opposite sides of the intermediate section 14 at the same longitudinal position. With this design, the intermediate section 14 can be deflected in one of two opposing directions. As would be recognized by one skilled in the art, other anchor positions could also be used in accordance with the invention. For example, the puller wires 64 could be anchored at different longitudinal positions, either on the same side of the intermediate section or on different sides. Such an arrangement would permit the user to create compound curves by simultaneous manipulation of the puller wires.

Longitudinal movement of a puller wire 64 relative to the catheter body 12 results in deflection of the intermediate section 14 in the direction of the side to which that puller wire is anchored. Such longitudinal movement is accomplished by suitable manipulation of the control handle 16. Any suitable control handle 16 capable of manipulating two different puller wires can be used in accordance with the invention. Depending on the arrangement and anchor positions of the puller wires, it may be desirable for the control handle to be capable of selective longitudinal movement of the puller wires so that the puller wires are not both simultaneously moved in the proximal direction. Such a design is particularly suitable for catheters like that depicted where the puller wires 64 are anchored on opposite sides of the intermediate section 14 at approximately the same longitudinal position. With such a design, simultaneous proximal movement of both puller wires would result in forces in opposing directions so that deflection of the intermediate section 14 would not occur. Examples of bidirectional control handles useful for the present invention are disclosed in U.S. Pat. Nos. 6,123,699, 6,171,277, 6,183,435, 6,183,463, 6,198,974, 6,210,407, and 6,267,746, the disclosures of which are incorporated herein by reference.

Figure 9:
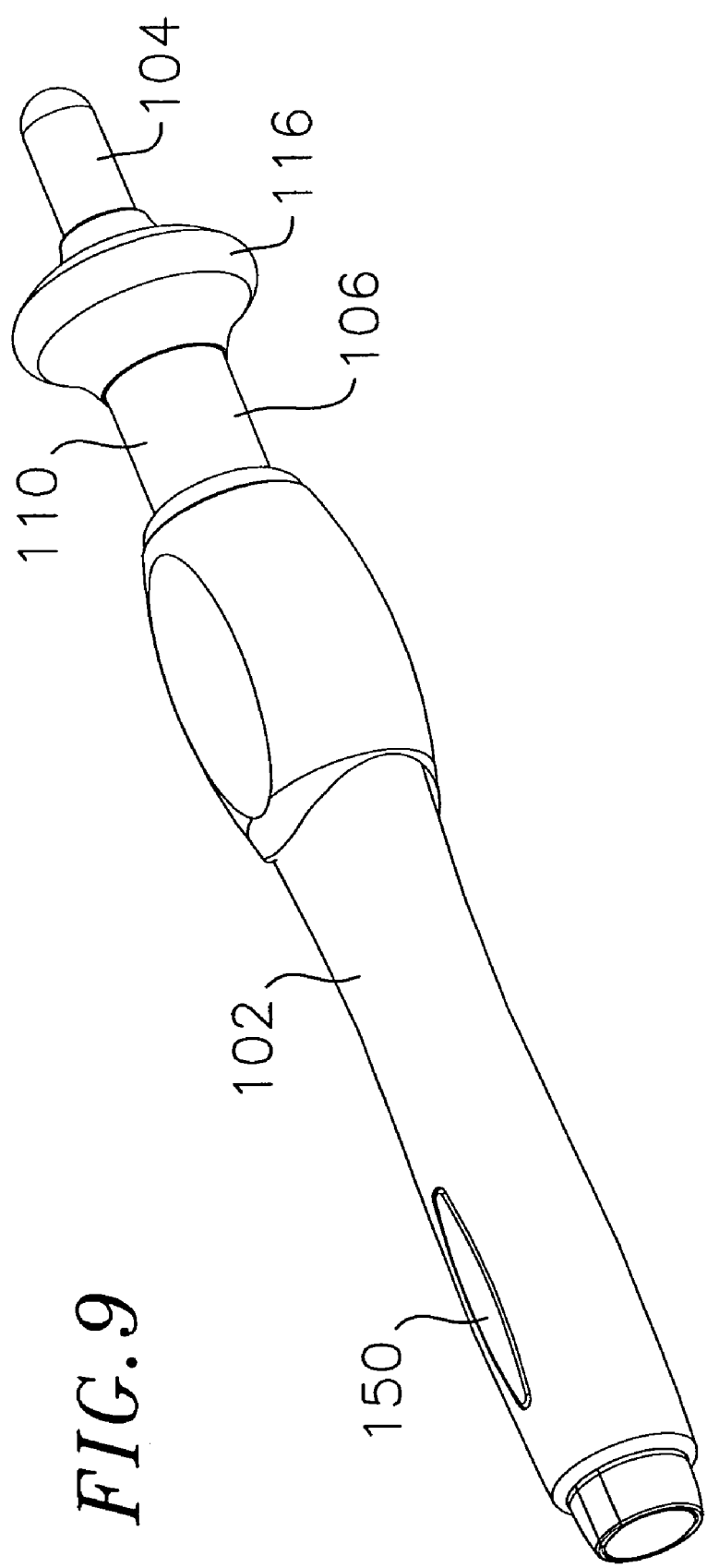
FIG. 9 is a perspective view of a handle in accordance with the invention.
Figure 10:
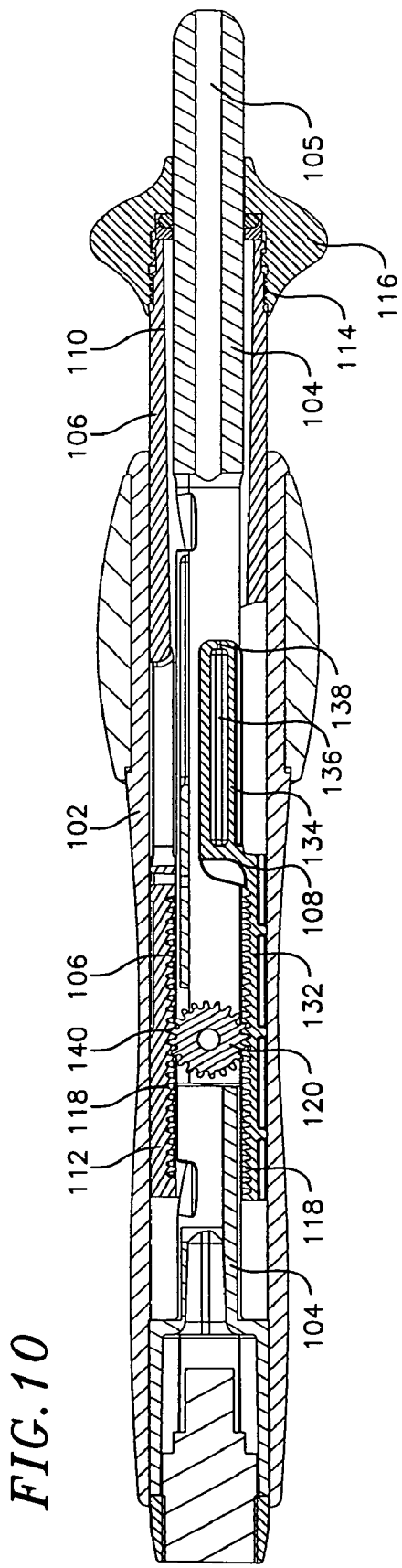
FIG. 10 is a side cross-sectional view of the handle of FIG. 9.
Figure 11:
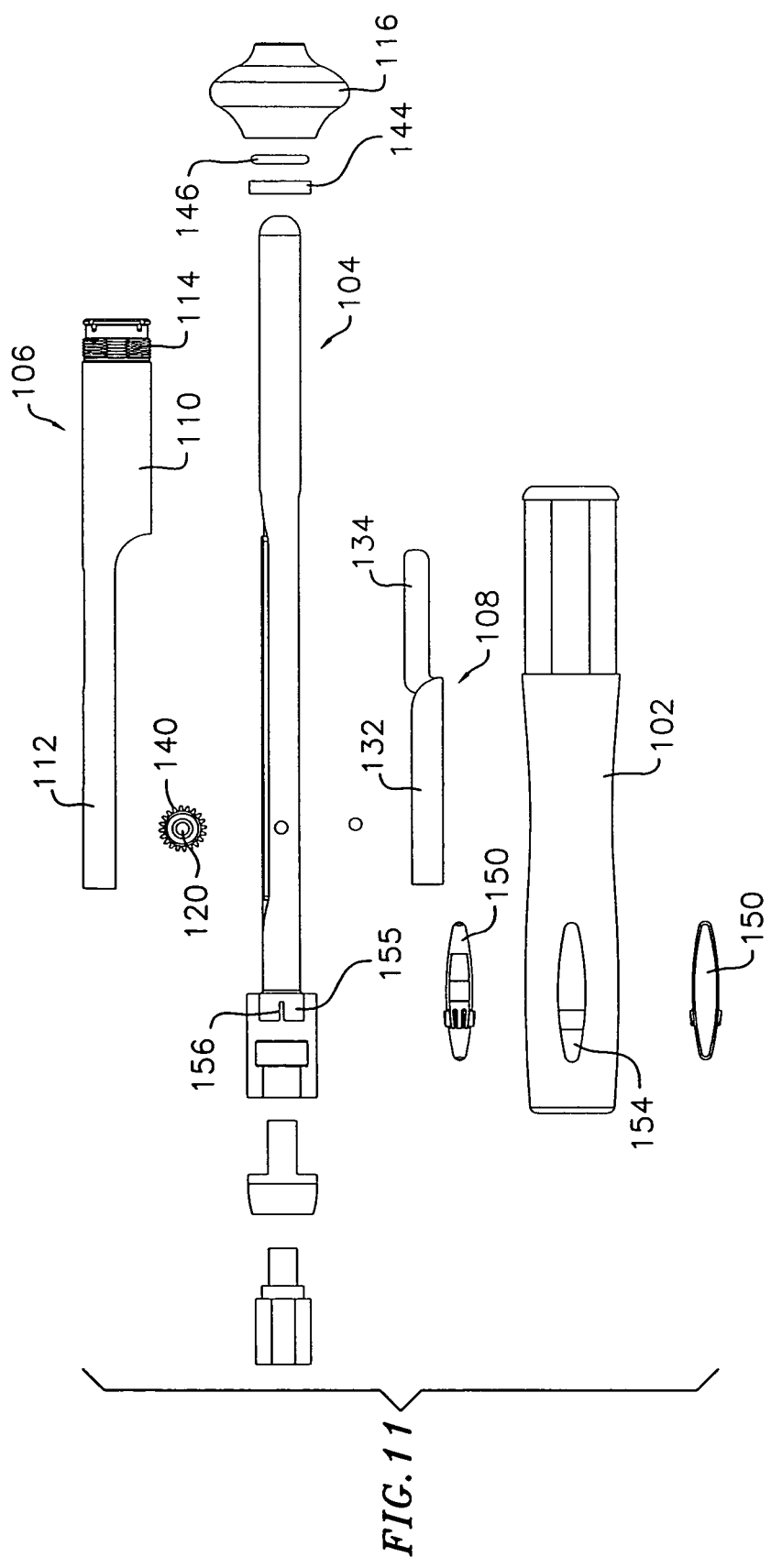
FIG. 11 is a side schematic view of the components of the handle of FIGS. 9 and 10 when the handle is not assembled.

A exemplary control handle 16 for use in connection with the present invention is depicted in FIGS. 9 to 11. The control handle 16 comprises a generally-hollow, preferably generally-tubular, handle housing 102 having a longitudinal axis and proximal and distal ends and a generally tubular core 104 extending within the housing along its longitudinal axis. The core 104 is generally tubular along its length and has proximal and distal ends that extend beyond and outside the proximal and distal ends, respectively, of the housing 102. The catheter body 12 is fixedly attached in a passage 105 at the distal end of the core 104 by means of a glue joint and shrink sleeve, as is known to those skilled in the art. The puller wires 64, lead wires 50 and other cables, wires or tubes that extend through the catheter body extend through the passage 105 in the core 104.

Figure 13:
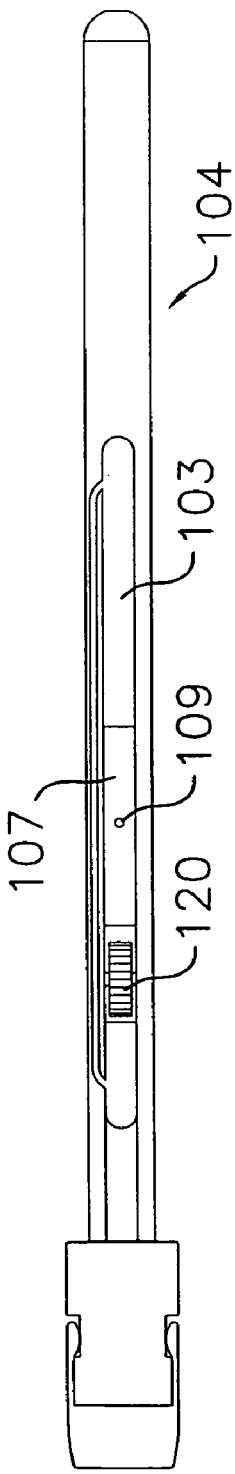
FIG. 13 is an alternative view of the core of the handle of FIGS. 9 to 11.

The core 104, as shown in more detail in FIG. 13, comprises two ovular slots 103 on opposite sides of the core that extend a portion of the length of the core, the functions of which are described in more detail below. A support member 107 is provided within the core 104 to add structural support to the core, and a small hole 109 is provided in the support member 107, the purpose of which is described below.

A primary piston 106 and a secondary piston 108 are mounted within the housing 102 generally in surrounding relation to the core 104, as described in more detail below. As shown best in FIG. 11, the primary piston 106 has a tubular distal region 110 and a proximal region 112 that has a generally semi-circular cross-section. As used herein, "generally semi-circular cross-section" refers to a generally-curved cross-section that may be greater or less than a semi-circle. The tubular distal region 110 is slidably mounted around the core 104 so that it completely surrounds the core. The proximal region 112 is shaped so that its inner surface fits generally against the tubular core 104, but only partially surrounds the core. When the handle 16 is assembled, a portion of distal region 110 extends outside the distal end of the housing 102. The distal region 110 of the primary piston 106 comprises threading 114 for mounting a thumb control 116 having corresponding internal threading (not shown) onto the primary piston. The inner surface of the proximal region 112 of the primary piston 106 comprises a series of teeth 118, which interact with a circular gear 120, described in more detail below.

Figure 12:
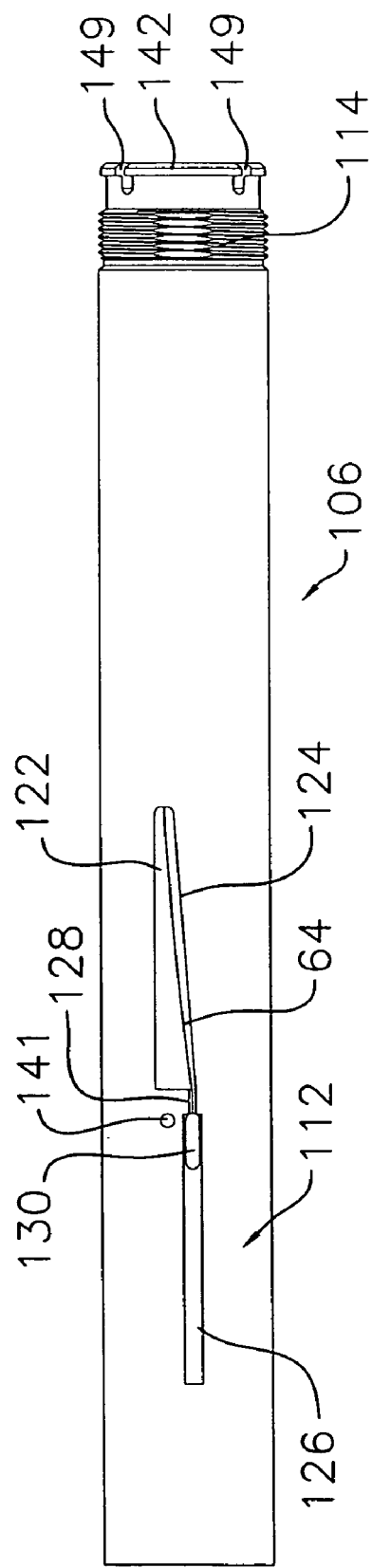
FIG. 12 is an alternative view of the primary piston of the handle of FIGS. 9 to 11.

FIG. 12 shows the primary piston 106 with the outer surface of the proximal region 112 turned toward the viewer. As shown best in FIG. 12, the proximal region 112 of the primary piston 106 is provided with a mechanism for anchoring one puller wire 64 to the primary piston. In the depicted embodiment, the proximal region 112 of the primary piston 106 comprises a generally trapezoidal opening 122 having a long slanted edge 124. The opening 122 extends through the primary piston 106. A channel 126, which only extends a part of the way through the outer surface of the proximal piston 106, is provided proximal to the opening 122. A small groove 128, having a width less than that of the channel 126, connects the channel to the opening 122. One puller wire 64 extends through the passage 105 in the core 104, out through one of the ovular slots 103 in the core, out through the opening 122 in the primary piston 106, through the small groove 128, and into the channel 126. The proximal end of the puller wire 64 is anchored in the channel 126 by means of a puller wire anchor 130, which preferably comprises a short piece of hypodermic stock that is fixedly attached, i.e., by crimping, to the proximal end of the puller wire 64 after it has passed through the small groove 128. The puller wire anchor 130 has a diameter greater than the width of the small groove 128 and thus prevents the proximal end of the puller wire 64 from being pulled through the small groove. The length of the opening 122 is preferably limited such that, when the primary piston 106 is in its most distal position relative to the housing 102, the opening does not extend outside the housing. However, the opening 122 is preferably long enough so that the puller wire 64 extends through the opening at an angle rather than bending or kinking. The opening 122 can have any other size or shape as desired so long as it permits passage of the puller wire 64. Other mechanisms for anchoring the puller wire 64 to the primary piston 106 would be recognized by one skilled in the art and can be used in accordance with the invention.

As shown in FIG. 11, the secondary piston 108 has a proximal region 132 having a generally-semicircular cross-section with a generally rectangular stem 134 extending distally therefrom. The proximal region 132 of the secondary piston 108 is shaped so that its inner surface fits generally against the tubular core 104, in a manner similar to the proximal region 112 of the primary piston 106. In a particularly preferred embodiment, the proximal region 132 of the secondary piston 108 and the proximal region 112 of the primary piston 106 contact each other and together surround the core 104. The inner surface of the proximal region 132 of the secondary piston 108, like the primary piston 106, comprises a series of teeth 118, which interact with the circular gear 120, described further below.

The stem 134 of the secondary piston 108 is shaped to slidably fit within one of the slots 103 of the core 104, as shown in FIG. 10. When the secondary piston 108 is moved distally, the stem 134 comes into contact with the distal end of the slot 103 in which it is mounted, controlling the extent of distal movement of the secondary piston. On one side, the stem 134 has a longitudinal channel 136 along its length, which terminates in a small longitudinal groove 138 having a width smaller than the width of the longitudinal channel. The second puller wire 64 extends through the passage 105 in the core 104, through the small longitudinal groove 138, and into the longitudinal channel 136. As with the primary piston, this puller wire 64 is anchored in the longitudinal channel 136 by means of a puller wire anchor (not shown) having a diameter greater than the width of the small longitudinal groove 138, thus preventing the proximal end of the puller wire 64 from being pulled through the small groove. Preferably, each puller wire 64 is anchored to a piston 106 or 108 in a position as close to the longitudinal axis of the core 104 as possible.

A circular gear 120 having teeth 140 about its circumference is mounted in the core 104, preferably by means of a dowel pin (not shown) or the like. The teeth 140 of the circular gear 120 are aligned with the teeth 118 on the inner surfaces of the primary piston 106 and secondary piston 108. Accordingly, distal movement of the primary piston 106 results in proximal movement of the secondary piston 108, and proximal movement of the primary piston results in distal movement of the secondary piston. Thus, when the thumb control 116 is moved distally relative to the handle housing 102 and core 104, the primary piston 106 is also moved distally, and the secondary piston 108 is correspondingly moved proximally. The puller wire 64 attached to the secondary piston 108 also is pulled proximally, causing the intermediate section 14 to deflect in the direction of the side of the intermediate section to which that puller wire is anchored. The puller wire 64 attached to the primary piston 106, however, does not compress; instead the puller wire 64 and puller wire anchor 130 are provided free movement in the channel 126.

Conversely, when the thumb control 116 is moved proximally relative to the handle housing 102 and core 104, the primary piston 106 is also moved proximally and the secondary piston 108 is correspondingly moved distally. The puller wire 64 attached to the primary piston 106 also is pulled proximally, causing the intermediate section 14 to deflect in the direction of the side of the intermediate section to which that puller wire is anchored. The puller wire 64 and puller wire anchor 130 mounted in the secondary piston 108 are permitted free movement within channel 136, and thus the puller wire is not compressed.

In the depicted embodiment, when the catheter is in the neutral position, i.e., when the intermediate section 14 is not deflected, the primary piston 106 and secondary piston 108 are positioned so that the circular gear 120 is located at the midpoint of the teeth 118 on each piston. Accordingly, both pistons 106 and 108 can travel the same distance forward and backward. However, if desired, the pistons 106 and 108 can be positioned so that one of the pistons can travel a greater distance in a given direction than the other piston.

When assembling the catheter of the depicted embodiment, preferably the catheter body 12, intermediate section 14 and mapping assembly 17 are assembled first. Next, the puller wires 64 are cut. In the depicted embodiment, when the primary piston 106 and secondary piston 108 are in the neutral position, the distal end 134 of the secondary piston is distal to the proximal end 112 of the primary piston. Thus, the distal end of the puller wire 64 anchored to the primary piston 106 is proximal the distal end of the puller wire anchored to the secondary piston 108. Accordingly, the puller wires 64 are cut to be of different lengths, with the puller wire anchored to the primary piston 106 being longer than the puller wire anchored to the secondary piston 108. When the intermediate section 14 is not deflected, both puller wires 64 should be close to being in tension.

To assemble the handle so that the puller wires 64 are properly aligned, a hole 141 is provided in the primary piston 106, as shown in FIG. 12. An assembly pin (not shown) is placed through the hole 141 in the primary piston 106 and the hole 109 in the support member 107 of the core 104, described above. This position corresponds to the neutral position of the handle, i.e., where the tip section is not deflected. The puller wire anchor 130 is then positioned in the channel 126 of the primary piston 106. The catheter body 12 is pulled until there is just a small amount of tension on that puller wire, and then the catheter body is glued in place to the core 104. The assembly pin is then removed.

When a physician is performing a procedure using the above-described catheter, it is desirable for the physician to be able to determine when the catheter is in the neutral position, i.e., when the tip section is not deflected. Accordingly, in a preferred embodiment, the center teeth of the primary piston are angled or skewed. The user can hear and feel when the teeth of the circular gear come into contact with the angled center teeth, notifying the user that the catheter is in the neutral position.

In an alternate design, as shown in FIGS. 18 and 19, the primary piston 106 comprises a tab 160 at its proximal end that extends radially outwardly. The tab 160 is formed on a finger 161 that is separated from the proximal end of the primary piston 106 by a slot 163 to provide the finger 161 with some flexibility. The housing 102 has a groove 162 on its inside surface. The groove 162 is positioned so that the tab 160 is aligned with the groove when the catheter is in the neutral position. As the primary piston 106 is slid longitudinally relative to the housing 102, the tab 160 interacts with the groove 162, which can be heard and felt by the user, indicating to the user that the catheter is in the neutral position. The flexibility of the finger 161 permits the tab 160 to fit within the housing 102 when it is not aligned with the groove 162 and to more easily slide in and out of the groove.

Figure 20:
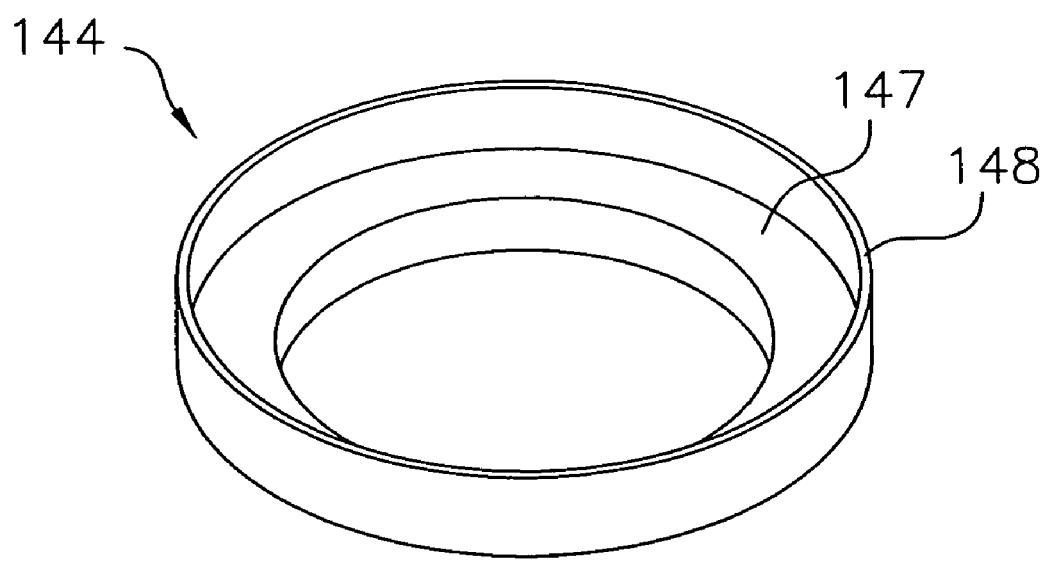
FIG. 20 is a perspective view of a washer according to the invention.
Figure 21:
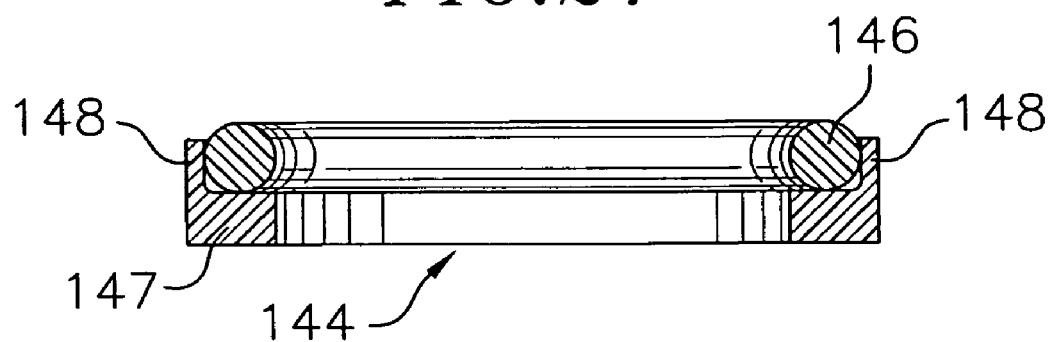
FIG. 21 is a cross-sectional view of an o-ring mounted in a washer according to the invention.

In a preferred embodiment, a washer 144 is mounted about the core 104 at the distal end of the primary piston 106. As shown in FIGS. 20 and 21, the washer 114 comprises a flat, O-shaped proximal ring 147 with an outer edge and an inner edge. An outer wall 148 extends distally from the outer edge of the proximal ring. By this design, a portion of the proximal end of the washer 144 is closed, but the distal end is open. The washer is preferably made out of the same material as the handle housing.

A flexible o-ring 146, made of plastic, rubber or the like, is provided having an outer surface, an inner surface, a proximal surface and a distal surface. The o-ring 146 sits in the open distal end of the washer 144 so that its proximal surface is in contact with the distal surface of the proximal ring of the washer, its outer surface is in contact with the outer wall 148, and its inner surface is in contact with the core 104.

With this design, when the thumb control 116 is screwed onto the proximal piston 106, it compresses the o-ring 146 into the washer 144, forcing the inner surface of the o-ring against the core 104. The user can adjust the tension on the thumb control 116 by screwing or unscrewing the thumb control, thus adjusting the pressure of the thumb control on the o-ring 146. Alternatively, the washer 144 can be integral with the distal end of the primary piston 106. In other words, the distal end of the primary piston 106 can be designed to incorporate a region into which the o-ring 146 can fit to perform the same function, e.g., having a proximal ring and an outer wall extending distally from the proximal ring.

In a particularly preferred embodiment, an additional mechanism is provided to prevent the user from completely unscrewing the thumb control 116 when adjusting the tension. As shown in FIG. 12, the distal end of the primary piston 106 comprises a circumferential lip 142. A corresponding circumferential groove (not shown) is provided inside the thumb control 116. The outer diameter of the lip 142 is greater than the inner diameter of the thumb control 116, but less than the inner diameter of the circumferential groove of the thumb control. Cuts 149 are provided about the circumference of the lip 142 to provide flexibility to the lip so that the lip can be assembled into the circumferential groove. The length of the circumferential groove is greater than the length of the lip. Thus, the user can make adjustments to the tension of the thumb control 116, while maintaining the lip 142 within the circumferential groove. However, the interaction between the lip 142 and circumferential groove maintains the thumb control 116 in place over the primary piston 106.

In another preferred embodiment, a fastener 150 is provided to maintain the handle housing 102 in place over the core 104. FIGS. 14 to 17 show a preferred fastener 150 in accordance with the invention. The fastener 150 has a generally ovular (or jewel) shape. The top side, as shown in FIG. 14, is generally flat, but may be slightly curved to match the curved contour of the handle housing 102. The bottom side, as shown in FIGS. 15 to 17, comprises two inner prongs 152 and two outer prongs 153. The prongs 152 and 153 are received by the proximal end of the core 104, shown best in FIG. 11. Specifically, the proximal end of the core 104 comprises a recess 155 separated by a tab 156. The prongs 152 and 153 extend into the recess 155, and the inner prongs 152 fit tightly around the tab 156 to maintain the fastener 150 in place. The handle housing 102 comprises an opening 154 corresponding in size and shape to the fastener 150. When the handle 16 is assembled, the fastener 150 is snapped into place in the opening 154 of the handle housing 102, with the prongs 152 and 153 being received by the distal end of the core 104, keeping the handle housing in place over the core. The outer prongs 153 comprise outwardly extending ears 157. When the fastener is snapped into the opening 154 of the housing 102, the ears 157 extend under the opening to keep the fastener 150 in place in the handle housing. The fastener 150 also provides a means for engraving or labeling the handle 16. The fastener 150 can be provided with a design, trademark, or other insignia relevant to the catheter, thus making it unnecessary to manufacture the handle housing with the insignia directly thereon. The inventive fastener can be used with any catheter handle design having a hollow housing and a core member of some sort in the housing to which the housing is to be fixedly attached.

In use, a suitable guiding sheath is inserted into the patient with its distal end positioned at a desired mapping location. An example of a suitable guiding sheath for use in connection with the present invention is the Preface™ Braiding Guiding Sheath, commercially available from Cordis Webster (Diamond Bar, Calif.). The distal end of the sheath is guided into one of the atria. A catheter in accordance with the present invention is fed through the guiding sheath until its distal end extends out of the distal end of the guiding sheath. As the catheter is fed through the guiding sheath, the mapping assembly 17 is straightened to fit through the sheath. Once the distal end of the catheter is positioned at the desired mapping location, the guiding sheath is pulled proximally, allowing the deflectable intermediate section 14 and mapping assembly 17 to extend outside the sheath, and the mapping assembly 17 returns to its original shape due to the shape-memory of the support member 24. The mapping assembly 17 is then inserted into a pulmonary vein or other tubular region (such as the coronary sinus, superior vena cava, or inferior vena cava) so that the outer circumference of the generally circular main region 39 of the assembly is in contact with a circumference inside the tubular region. The mapping assembly 17 can be directed by deflecting the intermediate section using one or both puller wires 64. Preferably at least about 50%, more preferably at least about 70%, and still more preferably at least about 80% of the circumference of the generally circular main region is in contact with a circumference inside the tubular region.

The circular arrangement of the electrodes 36 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or the coronary sinus. Additionally, because the main region 39 preferably does not form a flat circle, but instead is somewhat helical, as shown in FIG. 4, it is easier for the user to guide the mapping assembly 17 into a tubular region.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A bidirectional mapping catheter comprising:
   an elongated flexible tubular catheter body having an axis and proximal and distal ends;
   a mapping assembly at the distal end of the tubular body having a preformed generally circular main region having an outer surface, proximal and distal ends and carrying a plurality of spaced apart electrodes, the mapping assembly further comprising a generally straight distal region extending generally tangentially to the generally circular main region;
   first and second puller wires, each puller wire having proximal and distal ends and extending through the tubular catheter body, the distal end of each puller wire being anchored at or near the distal end of the catheter body; and
   a handle connected to the proximal end of the catheter body, wherein the handle comprises:
      a handle housing;
      a tubular core;
      first and second pistons slidably mounted on the core, each of the pistons having a proximal region configured to partially surround the core, the proximal end of the first puller wire being anchored to the first piston and the proximal end of the second puller wire being anchored to the second piston;
      a spur gear rotatably mounted between the first and second pistons, whereby proximal movement of one piston results in rotational movement of the spur gear and distal movement of the other piston, thereby moving the respective puller wires longitudinally relative to the catheter body for deflection of the distal end of the catheter body.

2. A catheter according to claim 1, further comprising a longitudinally movable thumb control fixedly attached to the first piston and accessible from outside the handle housing.

3. A catheter according to claim 2, whereby proximal movement of the thumb control relative to the handle housing results in proximal movement of the first piston and first puller wire relative to the handle housing and catheter body, and further whereby distal movement of the thumb control relative to the handle housing results in distal movement of the first piston, causing proximal movement of the second piston and puller wire relative to the handle housing and catheter body.

4. A catheter according to claim 2, wherein the thumb control is mounted on the distal end of the first piston.

5. A catheter according to claim 2, further comprising a washer and an O-ring both mounted about the core at the distal end of the first piston, the washer and O-ring configured to provide tension on the thumb control.

6. A catheter according to claim 2, wherein distal movement of the thumb control results in distal movement of one piston and proximal movement of the other piston.

7. A catheter according to claim 1, wherein the spur gear is mounted in the core.

8. A catheter according to claim 1, wherein:
   the first piston has a tubular distal region that completely surrounds a distal region of the core;
   the proximal region of the first piston has a generally-semicircular cross-section that partially surrounds a proximal region of the core; and
   the proximal region of the second piston has a generally-semicircular cross-section that partially surrounds the proximal region of the core;
   whereby the proximal region of the second piston and the proximal region of the first piston contact each other and together completely surround the proximal region of the core.

9. A catheter according to claim 1, wherein each of the pistons has a series of teeth for interaction with the spur gear.

10. A catheter according to claim 9, wherein the spur gear is positioned substantially at a midpoint of the series of teeth of each piston when the catheter body is without deflection.

11. A catheter according to claim 1, wherein the puller wires are of different cut lengths.

12. A catheter according to claim 1, wherein each of the puller wires has an anchor to its respective piston and each of the pistons is configured with a channel in which its respective puller wire and anchor have free movement when the pistons are moved longitudinally relative to the catheter body for deflecting the catheter body.

13. A catheter according to claim 1, wherein each of the pistons has teeth for interaction with the spur gear, and center teeth of one of the pistons are angled or skewed so as to provide an audible signal to the user when the catheter body is without deflection.

14. A catheter according to claim 1, wherein each of the pistons has teeth for interaction with the spur gear, and center teeth of one of the pistons are angled or skewed so as to provide a tactile signal to a user when the catheter body is without deflection.

15. A catheter according to claim 1, wherein the first piston has a tab and the housing has a groove, whereby the tab interacts with the groove to provide a signal to a user when the catheter body is without deflection.

16. A catheter according to claim 1, wherein the handle housing includes a fastener received in an opening configured in the housing, the fastener configured to display a marking.

17. A bidirectional mapping catheter comprising:
an elongated flexible tubular catheter body having an axis and proximal and distal ends;
a mapping assembly at the distal end of the tubular body having a preformed generally circular main region having an outer surface, proximal and distal ends and carrying a plurality of spaced apart electrodes, wherein when the catheter is viewed from the side with the catheter body positioned at the top of the generally circular main region, the catheter body forms an angle with the generally circular main region ranging from about 75° to about 95°;
first and second puller wires, each puller wire having proximal and distal ends and extending through the tubular catheter body, the distal end of each puller wire being anchored at or near the distal end of the catheter body; and
a handle connected to the proximal end of the catheter body, wherein the handle comprises:
a generally-hollow handle housing having proximal and distal ends and inside and outside surfaces,
a generally tubular core extending longitudinally within the housing,
a generally-circular spur gear rotatably mounted within the handle housing, the spur gear having teeth about its outer circumference, and
first and second pistons slidably mounted on diametrically opposed sides of the spur gear and each having a proximal region in surrounding relation to the tubular core within the handle housing, each of the pistons having an interior edge generally facing the interior edge of the other piston and comprising a series of teeth along its interior edge that engage the teeth of the spur gear, whereby proximal movement of one piston results in rotational movement of the spur gear and distal movement of the other piston; and
a longitudinally movable thumb control fixedly attached to the first piston and accessible from outside the handle housing;
wherein the proximal end of the first puller wire is anchored to the first piston and the proximal end of the second puller wire is anchored to the second piston, whereby proximal movement of the thumb control relative to the handle housing results in proximal movement of the first piston and first puller wire relative to the handle housing and catheter body, and further whereby distal movement of the thumb control relative to the handle housing results in distal movement of the first piston, causing proximal movement of the second piston and puller wire relative to the handle housing and catheter body.

18. A catheter according to claim 17, wherein:
the distal end of the first puller wire is anchored to a first side of the catheter body such that longitudinal movement of the first puller wire relative to the catheter body results in deflection of the distal end of the catheter body in the direction of the first side of the catheter body; and
the distal end of the second puller wire is anchored to a second side of the catheter body different from the first side such that longitudinal movement of the second puller wire relative to the catheter body results in deflection of the distal end of the catheter body in the direction of the second side of the catheter body.

19. A catheter according to claim 17, wherein the distal end of the first puller wire is anchored proximal to the distal end of the second puller wire.

20. A bidirectional mapping catheter comprising:
an elongated flexible tubular catheter body having an axis and proximal and distal ends;
an intermediate section at the distal end of the catheter body;
a mapping assembly at the distal end of the tubular body having a preformed generally circular main region having an outer surface, proximal and distal ends and carrying a plurality of spaced apart electrodes;
a support member having proximal and distal ends, wherein the distal end of the support member is anchored in the mapping assembly and the proximal end of the support member is anchored in the intermediate section;
first and second puller wires, each puller wire having proximal and distal ends and extending through the tubular catheter body, the distal end of each puller wire being anchored at or near the distal end of the catheter body; and
a handle connected to the proximal end of the catheter body, wherein the handle comprises:
a handle housing;
a tubular core;
first and second pistons slidably mounted on the core, each of the pistons having a proximal region configured to partially surround the core, the proximal end of the first puller wire being anchored to the first piston and the proximal end of the second puller wire being anchored to the second piston;
a spur gear rotatably mounted between the first and second pistons, whereby proximal movement of one piston results in rotational movement of the spur gear and distal movement of the other piston, thereby moving the respective puller wires longitudinally relative to the catheter body for deflection of the distal end of the catheter body.

\* \* \* \* \*